United States Patent [19]
Freitas et al.

[11] Patent Number: 5,330,497
[45] Date of Patent: * Jul. 19, 1994

[54] LOCKING TROCAR SLEEVE

[75] Inventors: Michael W. Freitas, Irving; Fred A. Allgood, Fort Worth, both of Tex.

[73] Assignee: Dexide, Inc., Fort Worth, Tex.

[ * ] Notice: The portion of the term of this patent subsequent to Aug. 3, 2010 has been disclaimed.

[21] Appl. No.: 990,513

[22] Filed: Dec. 15, 1992

Related U.S. Application Data

[63] Continuation of Ser. No. 679,748, Apr. 25, 1991, Pat. No. 5,232,451, and a continuation-in-part of Ser. No. 440,199, Nov. 22, 1989, Pat. No. 5,122,122.

[51] Int. Cl.$^5$ ............................................. A61B 17/34
[52] U.S. Cl. ................................. 606/185; 604/164
[58] Field of Search ..................... 606/191–198, 606/184, 185; 604/105, 110, 164–167, 256, 264

[56] References Cited

U.S. PATENT DOCUMENTS

| | | | |
|---|---|---|---|
| 1,870,942 | 8/1932 | Beatty . | |
| 2,649,092 | 8/1953 | Wallace . | |
| 3,039,468 | 6/1962 | Price | 604/164 |
| 3,397,699 | 8/1968 | Kohl . | |
| 3,692,029 | 9/1972 | Adair . | |
| 3,713,447 | 1/1973 | Adair . | |
| 4,608,965 | 9/1986 | Anspach, Jr. et al. . | |
| 4,627,838 | 12/1986 | Cross et al. | 604/105 |
| 4,655,752 | 4/1987 | Honkanen et al. | 604/256 |
| 4,861,334 | 8/1989 | Nawaz | 604/164 |
| 4,995,868 | 2/1991 | Brazier | 604/105 |
| 5,002,557 | 3/1991 | Hasson | 606/191 |

Primary Examiner—Stephen C. Pellegrino
Assistant Examiner—William Lewis

[57] ABSTRACT

An improved trocar sleeve (10) is disclosed for use in laparoscopic surgery. The sleeve (10) is provided with an expanded mushroom hinge (20) at the first end (14) of the sleeve inserted into the abdominal cavity. The mushroom hinge (20) can be expanded within the abdominal cavity to abut against the inner surface of the abdominal wall (18) to hold the sleeve in place. A split seal (52) having a concave shape facing the first end (14) of the trocar sleeve (10) is provided to prevent loss of pressurized gas from within the abdominal cavity through the sleeve (10) as the pressure of the gas itself urges the first and second seal lips (78, 80) on opposite sides of the slit in the seal into sealing engagement. In a second embodiment, a member (138) is rotated relative to an end member (150) to actuate the mushroom hinge.

12 Claims, 6 Drawing Sheets

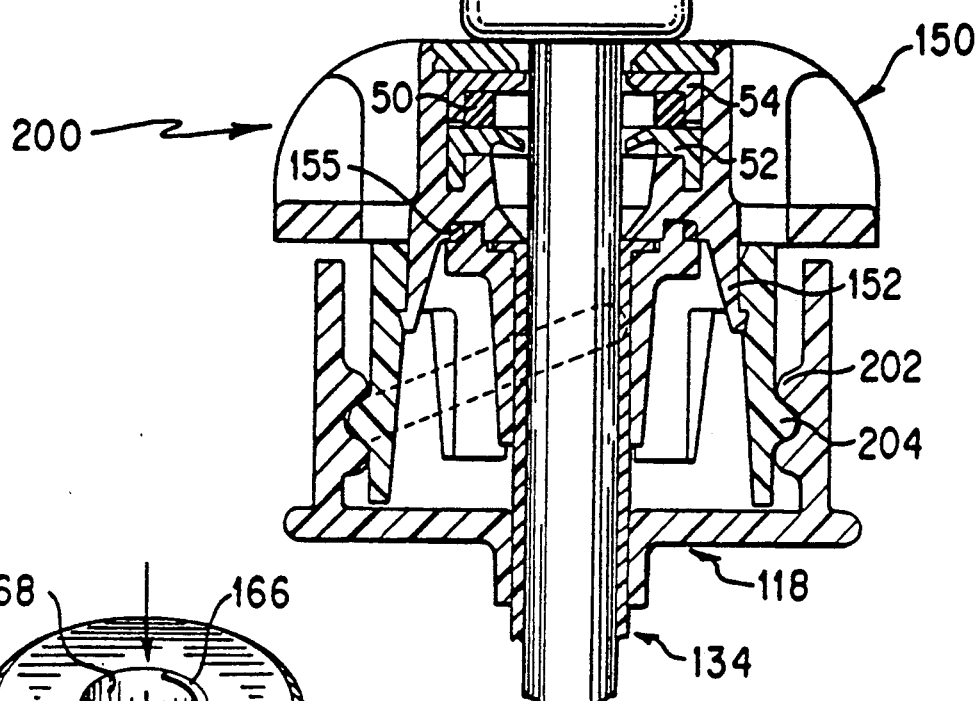
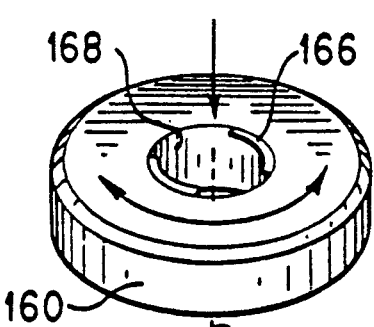
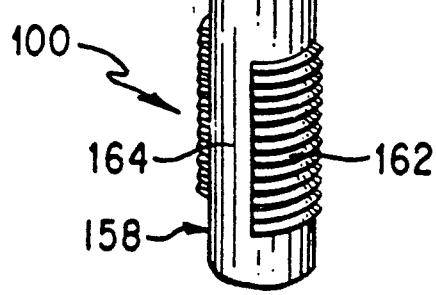

LOCKING TROCAR SLEEVE

CROSS REFERENCE TO RELATED APPLICATION

This is a continuation of co-pending application Ser. No. 07/679,748 filed on Apr. 25, 1991, now U.S. Pat. No. 5,232,451 and a continuation-in-part of pending U.S. patent application Ser. No. 440,199, filed Nov. 22, 1989, now U.S. Pat. No. 5,122,122.

TECHNICAL FIELD

The present invention relates in general to medical devices and more particularly relates to an improved trocar sleeve which can be inserted a short distance into the abdominal cavity and expanded to prevent the sleeve from sliding in and out of the incision.

BACKGROUND OF THE INVENTION

In the past few years, laparoscopic surgery has become increasingly important and widespread. In the past, when doing surgery within the abdominal cavity, a large incision through the abdominal wall was required to permit the surgeon to adequate view the area to be operated on. The development of the laparoscope, a small telescope utilizing fiber optic technology, allows the surgeon to view a cite to be operated on within the abdominal cavity with an incision only large enough to insert the laparoscope. With such a small incision required, laparoscopic surgery reduces the risk of infection to the patient and the extent of trauma to the body during the surgery. The surgery also reduces the chance of adhesions resulting from exposure of the interior of the body, a relative common occurrence in prior surgery.

In conducting laparoscopic surgery, a small incision is typically cut through the abdominal wall for insertion of a cannula. Pressurized carbon dioxide gas passes through the cannula to inflate the abdomen to create voids for passage of the laparoscope. After inflation, the cannula is removed.

A trocar, or sharp pointed instrument, is then used to form an incision through the abdominal wall which will be used for insertion of the laparoscope. A trocar sleeve is concentric with the trocar, with only the sharp end of the trocar exposed from the trocar sleeve. Thus, when the trocar is inserted through the abdomen wall, a first end of the trocar sleeve is pushed through the abdomen wall into the abdominal cavity. The trocar is withdrawn from both the abdomen and trocar sleeve, leaving the first end of the trocar sleeve within the abdominal cavity. The laparoscope, or other suitable apparatus, can then be inserted through the interior of the trocar sleeve into the abdominal cavity. One example of a trocar assembly is disclosed in U.S. Pat. No. 4,601,710 issued Jul. 22, 1986.

While such techniques have proven useful, several disadvantages remain. The trocar sleeve has a tendency to slide in and out of the incision in the abdominal wall, particularly when the surgeon is trying to move the laparoscopic instrumentation through the interior of the trocar sleeve into or out of the abdominal cavity. Further, seals are provided in the passage through the trocar sleeve to prevent the carbon dioxide gas from escaping the abdominal cavity. It is often difficult and time consuming to force the laparoscopic instrumentation or other device past these seals into the abdominal cavity.

Therefore, a need exists for an improved apparatus and method for performing such laparoscopic surgery.

SUMMARY OF THE INVENTION

An improved trocar assembly is provided for use in inserting a laparoscopic instrument into the abdominal cavity. The trocar assembly includes a trocar sleeve having a first end extending into the abdominal cavity through an incision in the abdominal wall. The first end has a first external diameter for passage through the incision. The trocar assembly further has structure for expanding a portion of the first end within the abdominal cavity so that the external dimension of the first end within the abdominal cavity is a larger, second external diameter. The expanded first end of the trocar sleeve abuts the inner abdominal wall about the incision to resist withdrawal of the trocar sleeve from the abdominal cavity.

In accordance with another aspect of the present invention, the trocar sleeve includes a first sleeve portion and a second sleeve portion, the sleeve portions being concentric. The first sleeve portion has a mushroom hinge thereon at the first end of the trocar sleeve. The structure for expanding the portion of the first end causes the first and second sleeve portions to move relative one another along their longitudinal axes to expand the mushroom hinge. The structure can include a spring for moving the sleeve portions relative one another and a latch mechanism for holding the spring in a compressed state with the first end of the trocar sleeve having the first external dimension. Release of the latch mechanism allows the spring to expand, causing the sleeve portions to move and expand the mushroom hinge. Alternatively, the structure can include at least one guide pin on one sleeve engaged with a guide surface on the other sleeve so that rotation of one sleeve relative to the other about the longitudinal axis causes the sleeve portions to move relative one another along their longitudinal axis.

In accordance with another aspect of the present invention, a trocar sleeve is provided which has a first end extending into the abdominal cavity through an incision in the abdominal wall. The trocar sleeve has a passage formed therethrough which extends from the abdominal cavity to the exterior. A seal is mounted in the trocar sleeve along the passage. The seal is formed of a resilient material and has a concave shape facing the first end of the trocar assembly within the abdominal cavity. A slit is formed in the seal, forming first and second seal lips on opposite sides of the slit. In the absence of a laparoscopic instrument, the pressure within the abdominal cavity urges the first and second lips together to form a seal at the slit. When a laparoscopic instrument is inserted through the passage, the first and second lips are resiliently deflected to permit passage of the instrument.

In accordance with another aspect of the present invention, a method for inserting a trocar sleeve through the abdominal wall for laparoscopic surgery is provided. The method includes the step of forming an incision through the abdominal cavity with a trocar and passing a first end of a trocar sleeve into the abdominal cavity. The first end of the trocar sleeve having a first external dimension for passage through the incision. The method further includes the step of expanding a portion of the first end within the abdominal cavity so that the external diameter of the first end within the cavity is expanded to a larger, second external dimension to abut the inner surface of the abdominal wall about the incision to resist withdrawal of the trocar sleeve from the abdominal cavity.

BRIEF DESCRIPTION OF THE DRAWINGS

Further features and advantages of the invention will become more apparent from the following Detailed Description and illustrated in the accompanying drawings, in which:

FIG. 9 is an exploded perspective view of an alternate stop locking mechanism;

FIG. 11 is a side view in cross-section of a modified trocar sleeve.

DETAILED DESCRIPTION

Figure 1:
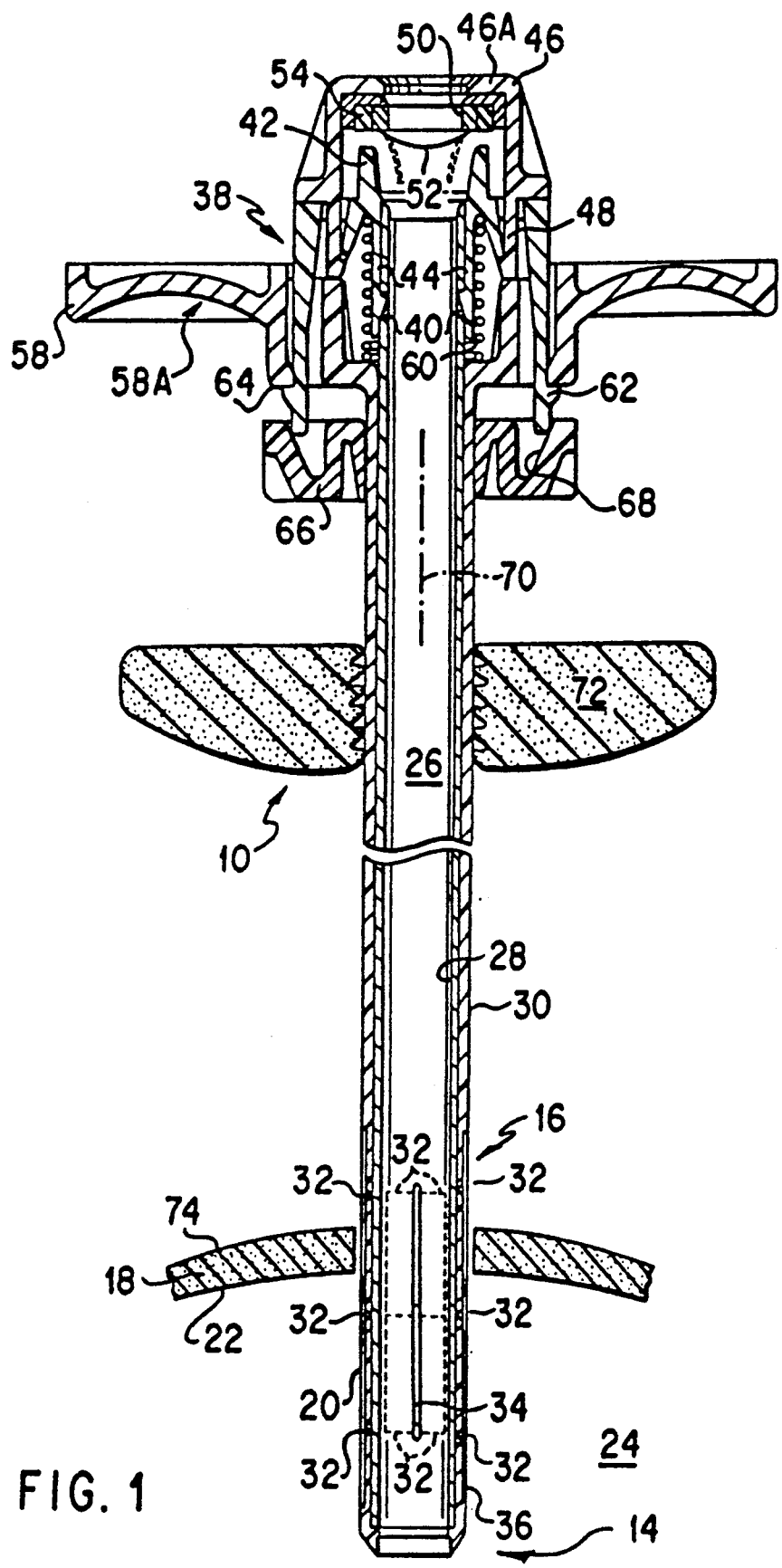
FIG. 1 is a side view of a trocar sleeve forming a first embodiment of the present invention prior to expansion.
Figure 2:
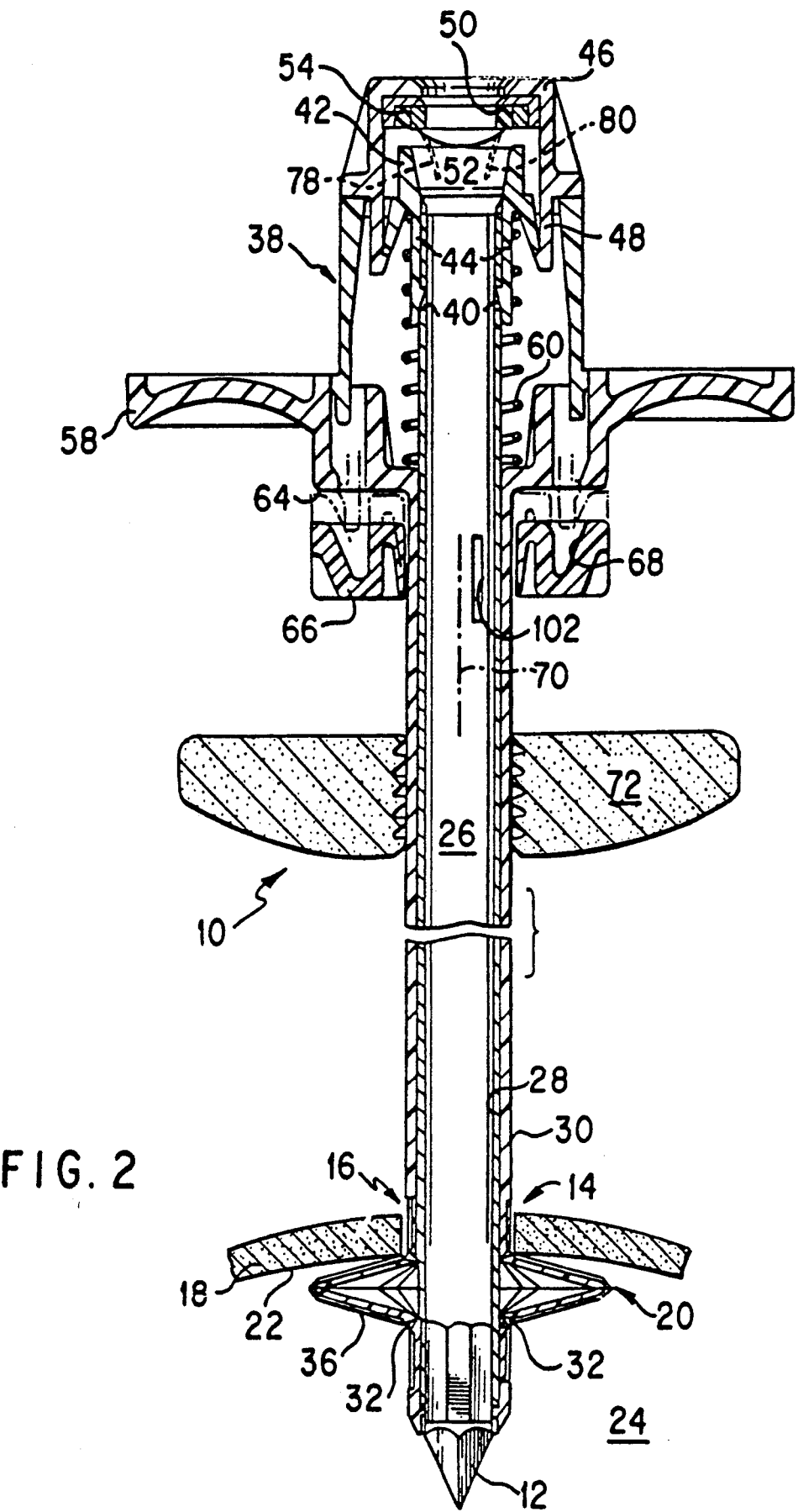
FIG. 2 is a side view of the trocar sleeve after expansion of the mushroom hinge.
Figure 3:
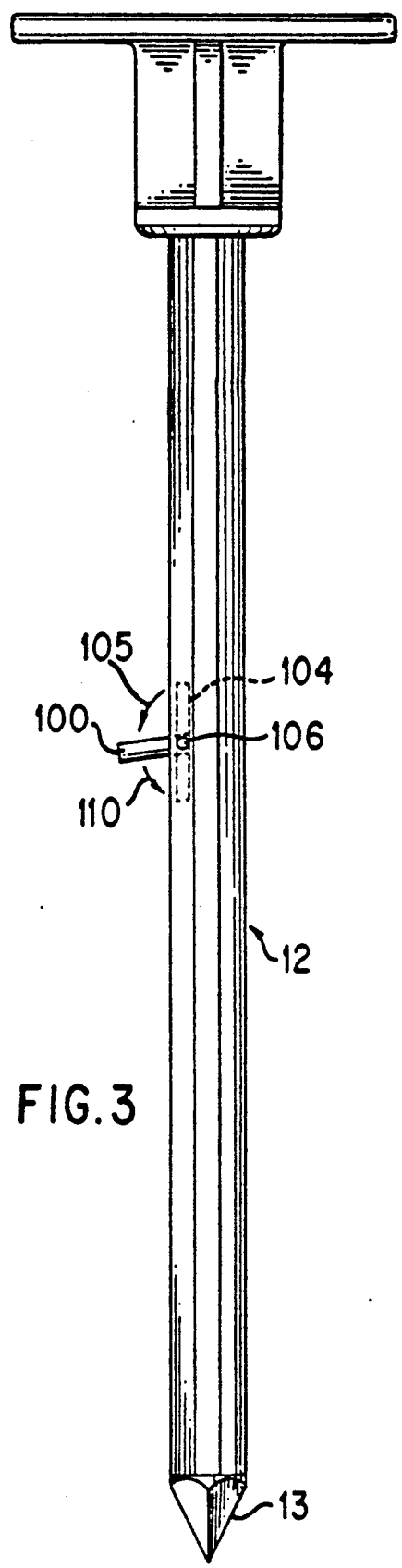
FIG. 3 is a side view of a trocar used with the trocar sleeve.

With reference now to FIGS. 1-3, a trocar sleeve 10 forming a first embodiment of the present invention is illustrated. With the assistance of a trocar 12, seen FIG. 3, a first end 14 of the sleeve 10 is inserted through an incision 16 in the abdominal wall 18 of a patient. The trocar 12 is inserted through passage 26 in the trocar sleeve so that only the sharp pointed end 13 extends from the first end 14 of sleeve 10. The pointed end of trocar 12 then is pushed through the abdominal wall along with first end 14. The sleeve 10 is secured therein by expansion of a mushroom hinge 20 which abuts the inside surface 22 of the abdominal wall about the incision 16 to prevent premature withdrawal of the trocar sleeve. After removal of trocar 12, laparoscopic instruments and the like can be inserted into the abdominal cavity 24 through passage 26 in the trocar sleeve 10.

With reference to FIGS. 1 and 2, the trocar sleeve 10 can be seen to include an inner cylindrical metal sleeve 28 and a concentric outer cylindrical plastic sleeve 30 preferably of polypropylene. The sleeves 28 and 30 are bonded or fastened together at the first end 14. Near the first end 14, the outer plastic sleeve 30 defines mushroom hinge 20 with a series of living hinges 32 about the circumference of the sleeve 30 separated by elongated slits 34. An outer elastic coating or sleeve 36, preferably of latex, overlies the living hinges 32 and slits 34 to cover the mushroom hinge 20. Coating or sleeve 36 insures that no body tissue is trapped between portions of the mushroom hinge, particularly when contracting the hinge for removal of the sleeve 10 from the patient.

At end 38 of the trocar sleeve opposite the first end, the metal sleeve 28 has a series of openings 40. A plastic end member 42 is secured to the metal sleeve 28 at end 38 by latches 44 received in the openings 40.

A plastic seal retaining cap 46 is, in turn, secured to the end member 42 by latches 48 on the cap. An O.D. seal 50, a split seal 52, and a pack ring 54 are confined between the end member 42 and cap 46 to prevent the pressurized gas within the abdominal cavity from escaping through the passage 26 in the metal sleeve 28 as will be described hereinafter. Seals 50 and 52 are preferably of silicon rubber.

A handle 58 is secured to the outer plastic sleeve 30 at end 38. A coil spring 60 acts between the end member 42 and the handle 58 to urge the handle 58 toward the first end of the trocar sleeve.

In the configuration illustrated in FIG. 1, the coil spring 60 is held in a compressed state between the end member 42 and the handle 58 as resilient latches 62 on the end member 42 are in contact with an end surface 64 of the handle.

A latch release 66 is received about the outer plastic sleeve 30 for movement relative the sleeve 30. The latch release 66 can be seen to have a conical camming surface 68 which can be moved into engagement with the ends of latches 62 to deflect the latches inward toward the axis 70 of the trocar sleeve 10. The latch release 66 can be activated by the surgeon directly, or, as an alternative, by providing a mechanism whereby withdrawal of the trocar after inserting the sleeve through incision 16 activates the latch release. The latches 62 will be deflected inward enough to release the handle 58 from the end member 42, which permits the spring 60 to expand to the position shown in FIG. 2. As the spring expands, the spring forces the handle 58, and attached outer plastic sleeve 30, toward the first end relative to the end member 42 and inner metal sleeve 28. This causes the portions of the plastic sleeve 30 at the living hinges to bend and expand the mushroom hinge 20, as seen in FIG. 2. It can be readily understood that the expanded mushroom hinge abuts the inside surface 22 of the abdominal wall 18 to resist removal of the trocar sleeve.

A dense rubber foam stop 72 can be frictionally engaged with the outer plastic sleeve 30. When the mushroom hinge has been expanded, the stop 72 can be slid downward along the plastic sleeve 30 toward the first end to contact the outer surface 74 of the abdominal wall 18 to resist movement of the trocar sleeve into the abdominal cavity.

It can be readily understood that the trocar sleeve 10 provides a stable platform for insertion of a laparoscopic instrument or the like through the sleeve 10 into the abdominal cavity through passage 56. The expanded mushroom hinge 20 also forms a good seal with the patient's abdominal wall 18 to prevent $CO_2$ loss. Any tendency for the trocar sleeve 10 to move relative the abdominal wall as the instrument is being inserted or removed will be greatly reduced by the expanded mushroom hinge 20 and stop 72.

When the trocar sleeve 10 is to be removed from the patient, surface 46A is pressed towards the handle 58 at surface 58A in a manner similar to a syringe to collapse the mushroom hinge 20 and compress the spring 60 until the latches 62 again latch against surface 64 of the handle 58 to allow removal of the trocar sleeve. The mushroom hinge 20 can be collapsed and removed without having to move stop 72.

Figure 4:
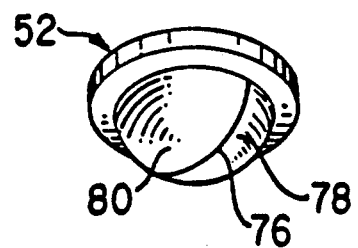
FIG. 4 is a perspective view of a seal within the trocar sleeve.

With reference now to FIGS. 1, 2 and 4, the mechanism for preventing gas from escaping the abdomen through the sleeve 10 will be described. When no laparoscopic instrument is inserted through the trocar sleeve 10, a split seal 52 prevents the escape of gas. The split seal 52 is formed of a resilient material which has a concave curvature facing the first end 14 of the trocar sleeve. A slit 76 is formed in the split seal which forms a first seal lip 78 and a second seal lip 80 on opposite sides of the slit 76. With the concave shape, the pressurized gas within the abdominal cavity acts to force the lips 78 and 80 together to form a tight seal to prevent the gas escape. When an instrument in inserted in end 38 of the trocar sleeve 10, the resilient lips 78 and 80 simply deflect away from the instrument, permitting the instrument to pass through the passage and into the abdominal cavity.

The O.D. seal 50 forms a seal against the outer cylindrical surface of an instrument as the instrument is inserted into the passage 26 of trocar sleeve 10. With the combination of the O.D. seal 50 and split seal 52, very little gas is lost as instruments are inserted and removed from the trocar sleeve 10.

Figure 5:
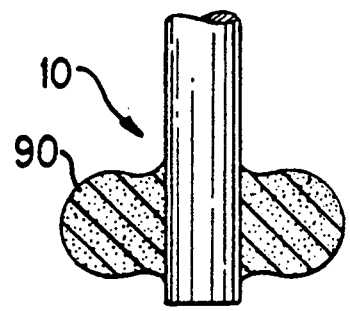
FIG. 5 is an illustrative view of a first modification of the trocar sleeve where an expanding sponge is used.

With reference to FIG. 5, a first modification of the trocar sleeve 10 is illustrated. In the first modification, an expanding sponge 90 replaced the mushroom hinge 20 at the first end of the trocar sleeve 10. The sponge 90 can be expanded in a manner similar to the mushroom hinge 20 to hold the trocar sleeve within the abdominal cavity.

Figure 6:
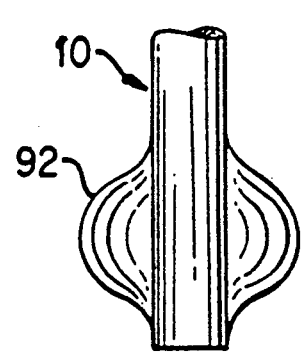
FIG. 6 is an illustrative view of a second modification of the trocar sleeve where an inflatable balloon is used.

With reference to FIG. 6, a second modification of trocar sleeve 10 is illustrated. In the second modification, an inflatable balloon 92 is mounted at the first end of the trocar sleeve which can be inflated to an expanded condition to secure the trocar sleeve within the abdominal cavity.

The sleeve 10 of the present invention reduces the frictional forces encountered by laparoscopic instruments being inserted into or removed from the sleeve as compared to prior designs. One reason for this advantage is that the entire sleeve 10 can be made shorter than past designs which required a longer length to insert through the abdominal wall to resist accidental removal of the sleeve from the patient. Another reason for the friction reduction is the use of efficient seals 50 and 52.

The trocar 12 can be used to automatically expand mushroom hinge 20 as the trocar is removed from sleeve 10. One possible mechanism for this is illustrated in FIGS. 2 and 3. A lever 100 can be pivoted to trocar 12 about hinge 106 and urged outwardly by a spring 104, The lever will be retracted into the trocar 12 as the trocar is inserted into the sleeve 10 to place the sleeve 10 through incision 16. When the trocar is removed from sleeve 10, the lever extends outward in the direction of arrow through a slot 102 in the sleeve so that the lever 100 contacts latch release 66. Further movement of trocar 12 would cause the release 66 to move upward and deploy the mushroom hinge. The lever 100 can be mounted to retract back into trocar 12 in the direction of arrow 110 after sufficient force has been exerted on trocar 12 to move release 66 to allow the trocar to be removed from sleeve 10.

In one possible construction of a sleeve in accordance with the teachings of the present invention, the inner diameter of the sleeve could be about 5 to 6 mm. with the diameter of the expanded hinge about 0.845 inches. The stroke of the sleeve 30 to activate the hinge could be ⅜ inches and sleeve 36 could be 10 mils thick.

Figure 7:
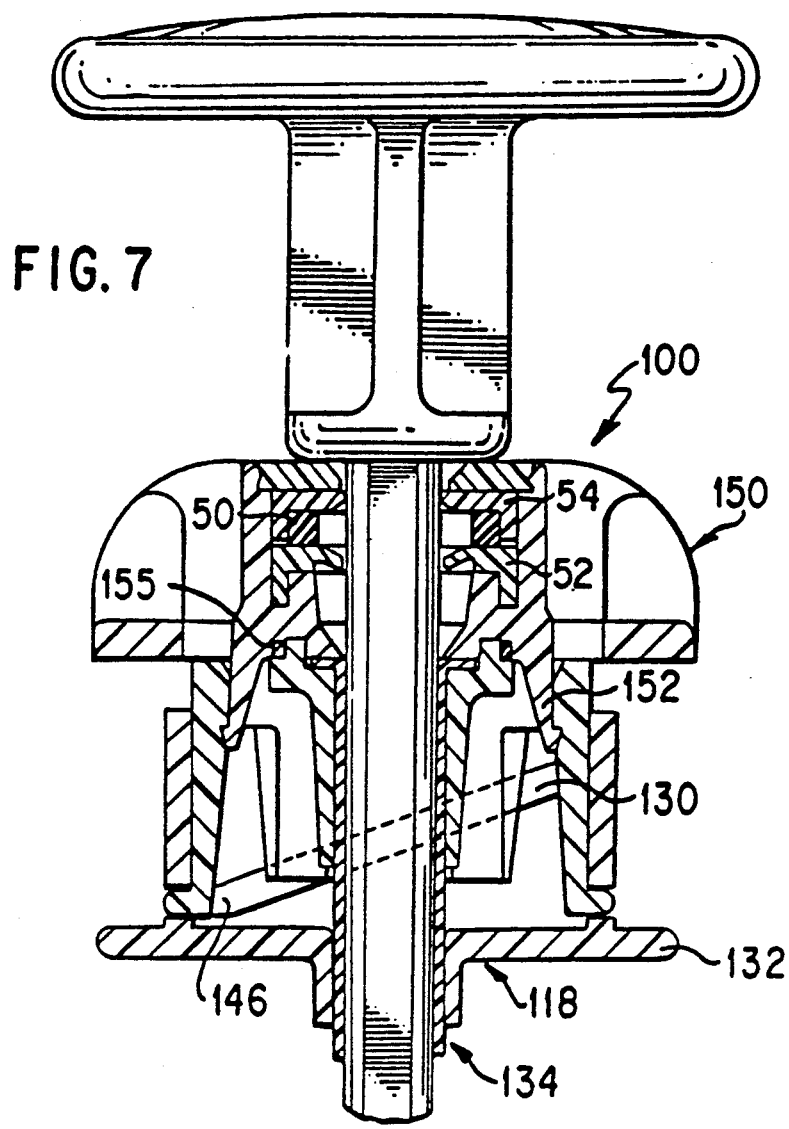
FIG. 7 is a side view in cross-section of a trocar sleeve forming a second embodiment of the present invention.
Figure 8:
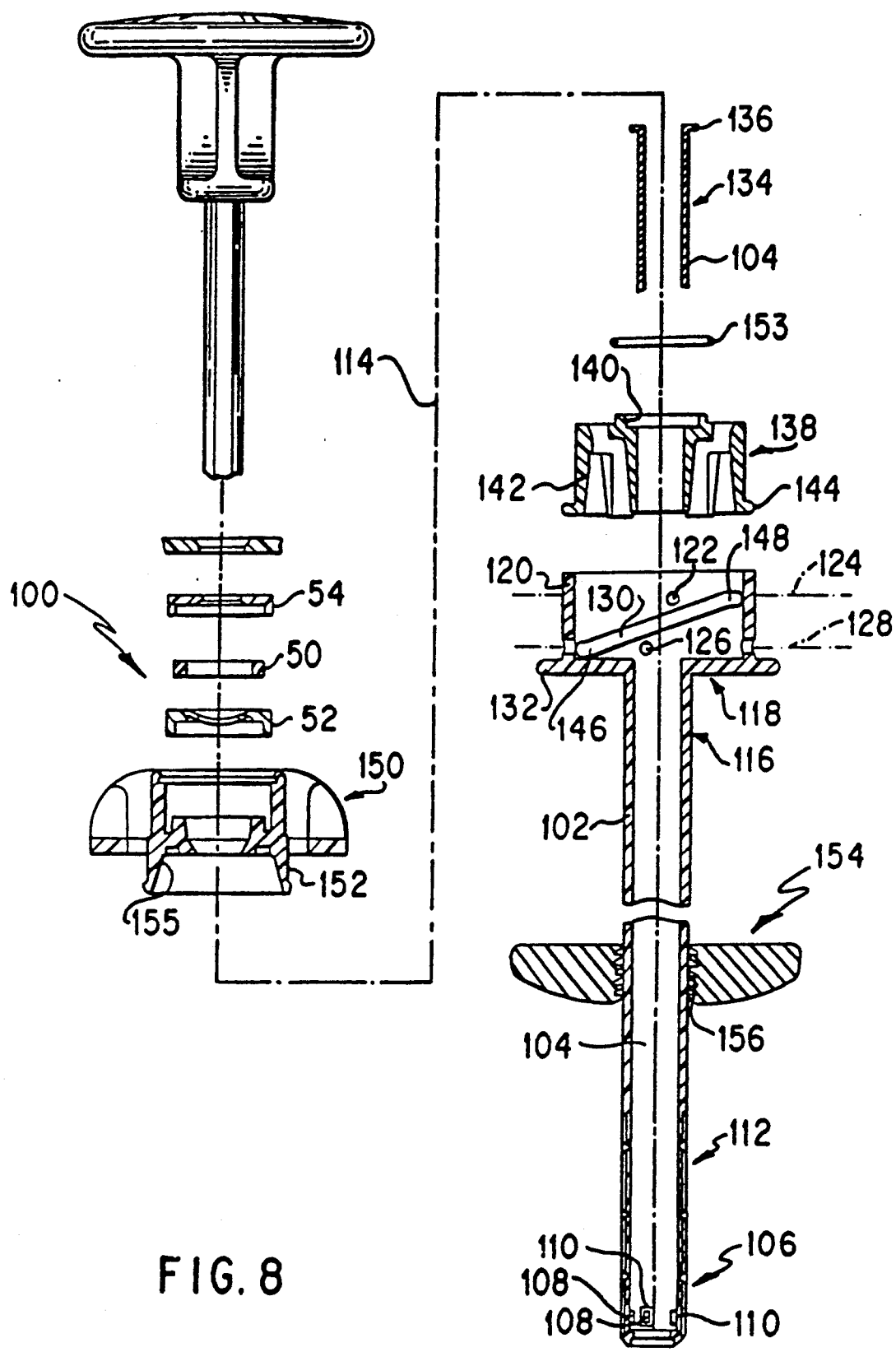
FIG. 8 is an exploded side view of the trocar sleeve of FIG. 7.

With reference now to FIGS. 7 and 8, a trocar 100 forming a second embodiment of the present invention is illustrated. The trocar 100 includes an outer cylindrical sleeve 102 and a concentric inner cylindrical sleeve 104. The sleeves 102 and 104 are secured together at a first end 106 of the trocar. The attachment is made by interlocking inwardly protruding lugs 108 on sleeve 102 which fit within similarly shaped openings 110 in the inner cylindrical sleeve 104. The outer cylindrical sleeve 102 is formed as a mushroom hinge 112 much as hinge 20. As with trocar 12, relative movement between the outer cylindrical sleeve 102 and the inner cylindrical sleeve 104 along their center axis 114 will expand the mushroom hinge 112 to secure the trocar 100 in place, or to retract the mushroom hinge for insertion or removal of the trocar.

The end 116 of the outer cylindrical sleeve 102 opposite the first end 106 flares outwardly to form a cylindrical portion 118. The cylindrical portion 118 includes a cylindrical wall 120 with a series of apertures 122 through the wall in a first plane 124 perpendicular to the axis 114 and a similar series of apertures 126 in a second plane 128 perpendicular the first axis. A series of helically directed guide slots 130 are also formed in the wall 120 which extend from one end in the first plane to an opposite end in the second plane. The cylindrical portion 118 also has a radially extending flange 132 which assists a surgeon to hold the cylindrical sleeve.

The end 134 of inner cylindrical sleeve 104 opposite the first end 106 forms an annular portion 136. A member 138 is slid over the inner cylindrical sleeve 104 so that the portion 136 of the inner cylindrical sleeve is received within an annular recess 140 in the member 138. The engagement between the portion 138 and recess 140 is sufficiently close to be essentially airtight, yet permit the member 138 to rotate about the axis 114 relative to the inner cylindrical sleeve 104. The member 138 also has a series of resilient arms 142 which extend into the cylindrical portion 118, with each arm 142 ending in a lug 144. Every other lug 144 is received in one of the guide slots 130. If the member 138 is rotated about axis 114 relative to the cylindrical portion 118, the interaction between the lugs and the guide slots 130 will cause the member 138, and sleeve 104, to move along axis 114. When the member 138 is turned so that lugs 144 abut a first end 146 of the guide slots, the mushroom hinge 112 is retracted and a trocar can be inserted or removed from the patient. When the member 138 is rotated so that lugs 144 are guided along slots 130 to the second end 148 of the slots, the member 138 and inner cylindrical sleeve 104 are translated along the axis 114 to cause the mushroom hinge 112 to expand to lock the trocar within the patient. The intermediate lugs 144, i.e., those lugs 144 not received in one of the guide slots 130, act as detents in the retracted or extended positions, with the intermediate lugs 144 engaging apertures 126 when the mushroom hinge 112 is retracted and the lugs 144 engaging the apertures 126 when the mushroom hinge is deployed.

An end member 150 is snap fit to member 138 with a plurality of resilient arms 152. An O-ring 153 seals between end member 150 and member 138. The sealing effect of the O-ring is enhanced by a conical seal surface 155 on member 150 which urges the O-ring into compression between members 138 and 150 to form an effective seal. The end member 150 mounts the O.D. seal 50, split seal 52 and packing ring 54 as used in trocar 12.

A significant advantage of the trocar 100 is the deployment and retraction of the mushroom hinge by rotating one part of the trocar relative to the other about its elongated axis. Since the forces necessary to insert the trocar in the patient and remove the trocar from the patient are generally along the axis 114, there is little opportunity in trocar 100 for an inadvertent deployment or retraction of the mushroom hinge during insertion or removal of the trocar. Further, as the laparoscopic instruments are also inserted or removed by exerting forces along the axis 114, these procedures will likewise entail little risk of inadvertent actuation of the trocar.

The dense rubber foam stop 154 is seen to have ridges 156 in contact with the outer surface of the outer cylindrical sleeve 102. These ridges are oriented to make the movement of the stop along the sleeve 102 toward the patient relatively easy so that the stop can be quickly pushed against the outer surface of the patient's skin. However, the ridges resist movement along the sleeve in the opposite direction to prevent inadvertent loosening of the trocar 100 from the patient.

With reference to FIG. 9, the trocar 100 is shown with a modified outer sleeve 158 and stop 160. The outer sleeve 158 is formed with a discontinuous thread 162 which defines two unthreaded grooves 164 along axis 114. The stop 160 has a similar noncontinuous thread 166 with grooves 168. By turning the stop 160 to one orientation relative to the sleeve 158, the threads of one part are in the grooves of the other part, which permits the stop to be moved freely along axis 114 relative to the outer sleeve. When the stop is properly positioned relative to the patient, the stop need only be rotated 90° to engage the threads of the stop and sleeve to lock the stop in the desired position.

Figure 10:
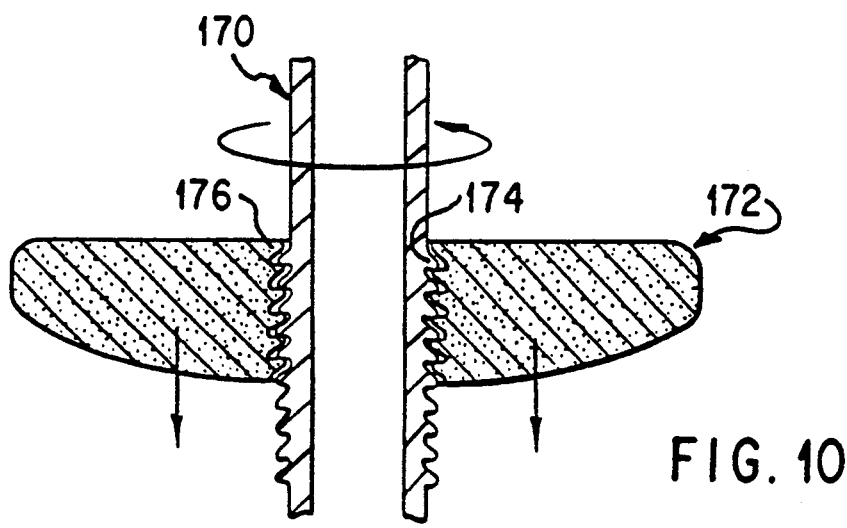
FIG. 10 is a side view of another alternate stop locking mechanism.

With reference now to FIG. 10, yet another modification of trocar 100 is illustrated which includes an outer cylindrical sleeve 170 and a stop 172. The outer cylindrical sleeve has a continuous thread 174 along its length. The stop has resilient rachet teeth 176 to engage the threads 174, which allows the stop to be easily moved in a direction along the axis 114 to move into engagement with the patient by the teeth 176 deflecting over the threads 174, but locks against threads 174 to resist removal. The threads 174 can be part of a continuous thread so that the stop can be backed off from the patient by rotating the stop to thread the stop back away from the patient.

Reference to FIG. 11 illustrates a trocar 200 which is a modification of trocar 100. Trocar 200 uses mating threads 202 on cylindrical portion 118 and threads 204 on member 138 to move sleeves 102 and 104 relative each other to activate the mushroom hinge. The threads have a pitch selected so that the desired axial movement between sleeves 102 and 104 can be achieved by rotating the threads less than one-half turn.

While the preferred embodiments of the present invention has been described in detail and shown in the accompanying drawings, it will be evident that various further modifications and uses not illustrated are possible without departing from the scope of the invention.

We claim:

1. An improved assembly used to transport an endoscopic instrument through an incision in a patient's body, while minimizing loss of gas used to inflate the body cavity during endoscopic procedures, the assembly comprising:
   a housing;
   an outer sleeve extending from the housing, with a plurality of hinges to expand radially within the cavity to resist withdrawal;
   an inner sleeve concentric with, and having a portion secured to, the outer sleeve to transport an endoscopic instrument;
   the outer sleeve having a proximate portion movable relative to the inner sleeve to expand or retract the hinges;
   actuator means to move one of the sleeves relative to the other, with user detectable detent means to signal a change in the radial position of the hinges by change in user feel;
   seal means to prevent gas flow through the interior of the assembly from the body cavity;
   stop means adapted to engage the exterior of the body to cooperate with the hinges when expanded to resist movement of the assembly and to minimize loss of gas between the outer sleeve and the incision.

2. The invention defined by claim 1 wherein the actuator means comprises a rotatable outer member coupled to an inner member, one of the members being connected to the outer sleeve for movement upward or downward to expand or retract the hinges.

3. The invention defined by claim 2 wherein the seal means further comprises an O.D. seal to seal against gas flow between the inner sleeve and the endoscopic instrument.

4. The invention defined by claim 3 wherein the seal means further comprises a closure seal to seal against gas flow through the inner sleeve when the endoscopic instrument is removed from the assembly.

5. The invention defined by claim 4 wherein the stop means comprises a dense, foam rubber annular ring to movably engage the outer sleeve.

6. The invention defined by claim 1 which further includes a pin on one of said members to engage and disengage a detent on the assembly to require change in user effort and signal the position of the hinges.

7. An improved assembly used to transport instruments through an incision in a patient's body, while preventing loss of gas used to inflate the body cavity during endoscopic procedures, the assembly comprising:
   a housing;
   an outer sleeve extending from the housing and having a plurality of radially expandable and retractable hinges adapted for insertion through the incision and expansion within the body cavity to prevent withdrawal;
   an inner sleeve concentric with the outer sleeve, with a portion secured to the outer sleeve distally of the hinges and with a sealed passage for insertion or removal of an endoscopic instrument without loss of gas from the body cavity;
   the outer sleeve having a proximate portion above the hinges able to move relative to the inner sleeve to expand or retract the hinges;
   an actuator coupled to at least one of the sleeves to move one of the sleeves relative to the other to retract or expand the hinges, and having position changes to indicate the status of the hinges, including detent that signal position by a change in user feel;
   at least one seal element disposed in the housing to prevent liquid or gas flow through the inner sleeve from the body cavity;
   a movable stop member disposed around the outer sleeve and adapted to engage the exterior of the body to cooperate with the expanded hinges to resist movement of the assembly and to prevent loss of gas between the outer sleeve and the incision.

8. The invention defined by claim 7 wherein the actuator comprises a rotatable outer member threaded to an inner member, one of the members being connected to the outer sleeve for movement upward or downward to expand or retract the hinges and to indicate the status of the hinges.

9. The invention defined by claim 8 wherein the seal element further comprises an O.D. seal to seal against gas flow between the inner sleeve and the endoscopic instrument.

10. The invention defined by claim 9 which further comprises a closure seal to seal against gas flow through the inner sleeve when the endoscopic instrument is removed from the assembly.

11. The invention defined by claim 10 wherein the stop member comprises a dense, foam rubber annular ring to frictionally and slidably engage the outer sleeve.

12. The invention defined by claim 8 which further includes a pin associated with one of said members and a detent on the assembly that engages or disengages to signal the position of the hinges.

* * * * *